United States Patent [19]
Jacobsen et al.

[11] Patent Number: 6,063,101
[45] Date of Patent: May 16, 2000

[54] STENT APPARATUS AND METHOD

[75] Inventors: Stephen C. Jacobsen; John Lippert; David L. Wells; Clark C. Davis; Kent Backman, all of Salt Lake City, Utah

[73] Assignee: Precision Vascular Systems, Inc., Salt Lake City, Utah

[21] Appl. No.: 09/196,797

[22] Filed: Nov. 20, 1998

[51] Int. Cl.$^7$ .................................................. A61M 29/00
[52] U.S. Cl. ............................................. 606/194; 606/108
[58] Field of Search ................................... 606/108, 194, 606/192, 198; 604/96

[56] References Cited

U.S. PATENT DOCUMENTS

| | | | |
|---|---|---|---|
| 5,129,910 | 7/1992 | Phan et al. | 606/108 |
| 5,292,331 | 3/1994 | Boneau . | |
| 5,354,279 | 10/1994 | Höfling . | |
| 5,571,086 | 11/1996 | Kaplan et al. | 606/194 |
| 5,674,278 | 10/1997 | Boneau . | |
| 5,882,335 | 3/1999 | Leone et al. | 606/108 |

*Primary Examiner*—Michael Buiz
*Assistant Examiner*—Kevin Truong
*Attorney, Agent, or Firm*—Thorpe, North & Western, LLP

[57] ABSTRACT

A stent for disposition in a body passageway or duct to maintain the duct walls apart, for example, to allow the flow of fluid therethrough, includes an elongate flexible support wire formed into an annular lattice having a central void, for disposition at a target location in the duct. Also included is an elongate flexible connecting wire joined at a distal end to the annular lattice and having a discontinuity for severing when supplied with a perturbation signal, a balloon catheter having an expandable section disposable in the void of the annular lattice so that when the expandable section is expanded, it forces the annular lattice radially outwardly to contact and hold apart the duct walls, and a fluid supply for supplying fluid to the expandable section of the balloon catheter to cause it to expand. A perturbation signal source is provided for supplying the perturbation signal to the discontinuity of the connecting wire to cause severance thereof.

21 Claims, 3 Drawing Sheets

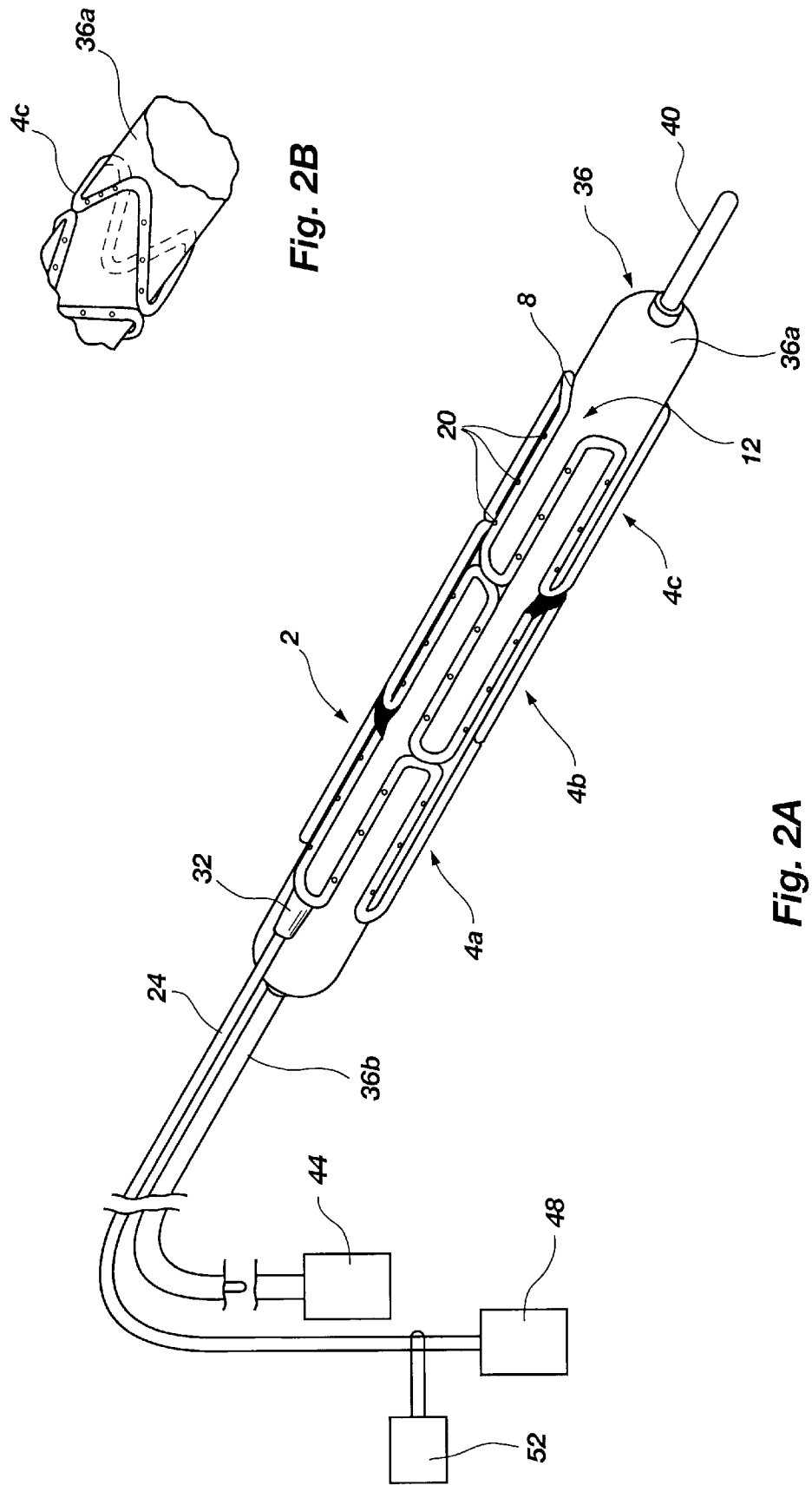

STENT APPARATUS AND METHOD

BACKGROUND OF THE INVENTION

This invention relates to devices and methods for maintaining a blood vessel or like passageways in an open condition and, if desired, for delivering medication to the blood vessel or passageway walls.

Vascular medical treatment procedures are known to include, among other things, occluding a blood vessel by thrombogenic devices, and maintaining the blood vessels open by use of a stent. Stents typically used in the past have consisted of a stainless steel tube section which includes selectively positioned gaps or openings which enable the section to be expanded (with a typically shortening of the length), for example, by a balloon catheter, after the section is positioned at the desired location in the blood vessel.

Problems with the above prior art stent, among other things, are that the length changes when the tubular section is expanded (the length shortened), and the length of the stent is limited since the greater is the length, the more difficult it is to deliver the stent to a target location in the blood vessel. That is, the stent being rigid, does not navigate well in the blood vessel, especially around tight corners. Further, since the described stent cannot be very long, numerous stents must be used for a diffuse diseased blood vessel.

A stent design which alleviates some of the above problems is disclosed in U.S. Pat. Nos. 5,292,331 and 5,674,278. This stent is comprised of a wire formed in a zig-zag pattern which extends in an annular configuration and which is compressed for disposition in a blood vessel and then expanded by a balloon catheter outwardly to hold the vessel walls apart.

A problem with the above and other unitary stents is that in the course of delivering them to a desired location in a blood vessel, the stents may become separated from the carrier/placement device, typically a balloon catheter, and drift downstream in the blood vessel. This, of course, could give rise to a dangerous situation in which the stent became lodged at a branch, bend, or at a distal narrowing in the vessel, and thus inhibit the flow of blood, This may require surgical intervention to remove the errant stent.

Besides the vascular medical treatment of maintaining blood vessels in an open condition, there are numerous situations where application of medications to an affected area of a vessel wall may be beneficial, for example, in treating arterial sclerosis, aneurysms or other weakening of the vessel wall, occlusive lesions, etc. Application of such medications may be done systemically by injecting medication into the vessel and then allowing the blood to carry the medication to the affected area. The problem with this approach is that high dosages of medication are required to ensure that some small portion reaches the affected area, and the high dosage may be harmful to other organs or body parts.

Another approach to treating diseases of vessel walls is to place a block before and after the affected area and then inject medications into the portion of the vessel between the two blocks. The problem with this approach is that blood flow is stopped for a certain amount of time and this, in itself, is dangerous.

Still another prior art approach is to thread a catheter through the blood vessel to the affected area and then either supply the medication through the catheter to the affected area, or supply the medication through a needle which itself is threaded through the catheter, pierce the vessel wall with the needle, and then supply the medication (see U.S. Pat. No. 5,354,279). The problem with simply supplying the medication via the catheter is that much of the medication is carried away in the blood and may adversely affect other organs.

A further prior art approach to supplying medication to a vessel wall involves the use of an inflatable sleeve positioned adjacent the affected area, where the sleeve includes an annular cavity holding the medication. When the sleeve is inflated to expand outwardly, the medication held in the cavity is placed into contact with the vessel walls and released thereinto. The problem with this approach is that the blood vessel again is blocked for a time and thus a gradual therapeutic regimen is not possible.

The placement of the stent can itself be a source of disease, by irritating the vessel wall at the points of contact. Also, thrombus can form on the stent causing a potentially fatal situation. The ability to deliver or release drugs or anti-thrombotic agents could reduce these problems.

SUMMARY OF THE INVENTION

It is an object of the invention to provide a stent which is easily deployable in a vasculature or other passageway to maintain the passageway in an open condition.

It is also an object of the invention to provide such a stent which may be maintained under the control of the user, and not become separated from the deploying device, until so desired by the user.

It is a further object of the invention to provide such a stent capable of delivering medication, therapeutic agents, and the like toward a blood vessel or other passageway wall.

It is still another object of the invention to provide such a stent which is non-occlusive and substantially non-inhibiting of blood flow or other fluids flowing in the passageway.

It is an additional object of the invention to provide such a stent which is capable of delivering medication substantially directly to a vessel or passageway wall.

The above and other objects are realized in an illustrative embodiment of a stent adapted for disposition in a blood vessel or other body passageway to maintain the passageway walls apart to allow the flow of blood or other fluids therethrough. This embodiment includes an elongate flexible support wire formed into an annular lattice having a central void, for disposition at a target location in the passageway, an elongate flexible connecting wire joined at a distal end to the annular lattice and having a discontinuity for severing when supplied with a perturbation signal, a balloon catheter having an expandable section disposable in the void of the annular lattice so that when the expandable section is expanded, it forces the annular lattice radially outwardly to contact and hold apart the passageway walls, a device for selectively expanding the expandable section of the balloon catheter, and a signal supply means for supplying a perturbation signal to the discontinuity of the connecting wire to cause severance thereof. With this structure, the stent may be delivered to the desired location and, since it is tethered by a connecting wire, control of the stent may be maintained until it is expanded at the target location to contact the passageway walls. Then, the perturbation signal may be supplied to the discontinuity of the connecting wire so that the connecting wire is severed, after which the connecting wire may be removed from the passageway.

In accordance with another aspect of the invention, the support wire and connecting wire are tubular to enable carrying medication, and the support wire includes perforations through which medication may flow from the hollow of the support wire. In use, after the lattice has been expanded outwardly to contact the passageway walls, medication may be supplied through the hollow of the connecting wire to the hollow of the support wire, to then flow through the perforations to contact the passageway walls for treatment.

Advantageously, the perforations are positioned to cause the medication to flow generally outwardly from the lattice to thereby contact the passageway walls, but could be positioned to cause the medication to flow in any desired direction.

BRIEF DESCRIPTION OF THE DRAWINGS

The above and other objects, features and advantages of the invention will become apparent from a consideration of the following detailed description presented in connection with the accompanying drawings in which:

FIGS. 2A and 2B are perspective, fragmented views of the stent of FIG. 1, with a balloon catheter in place in the central void of the stent shown in the collapsed and expanded conditions respectively;

DETAILED DESCRIPTION

Figure 1:
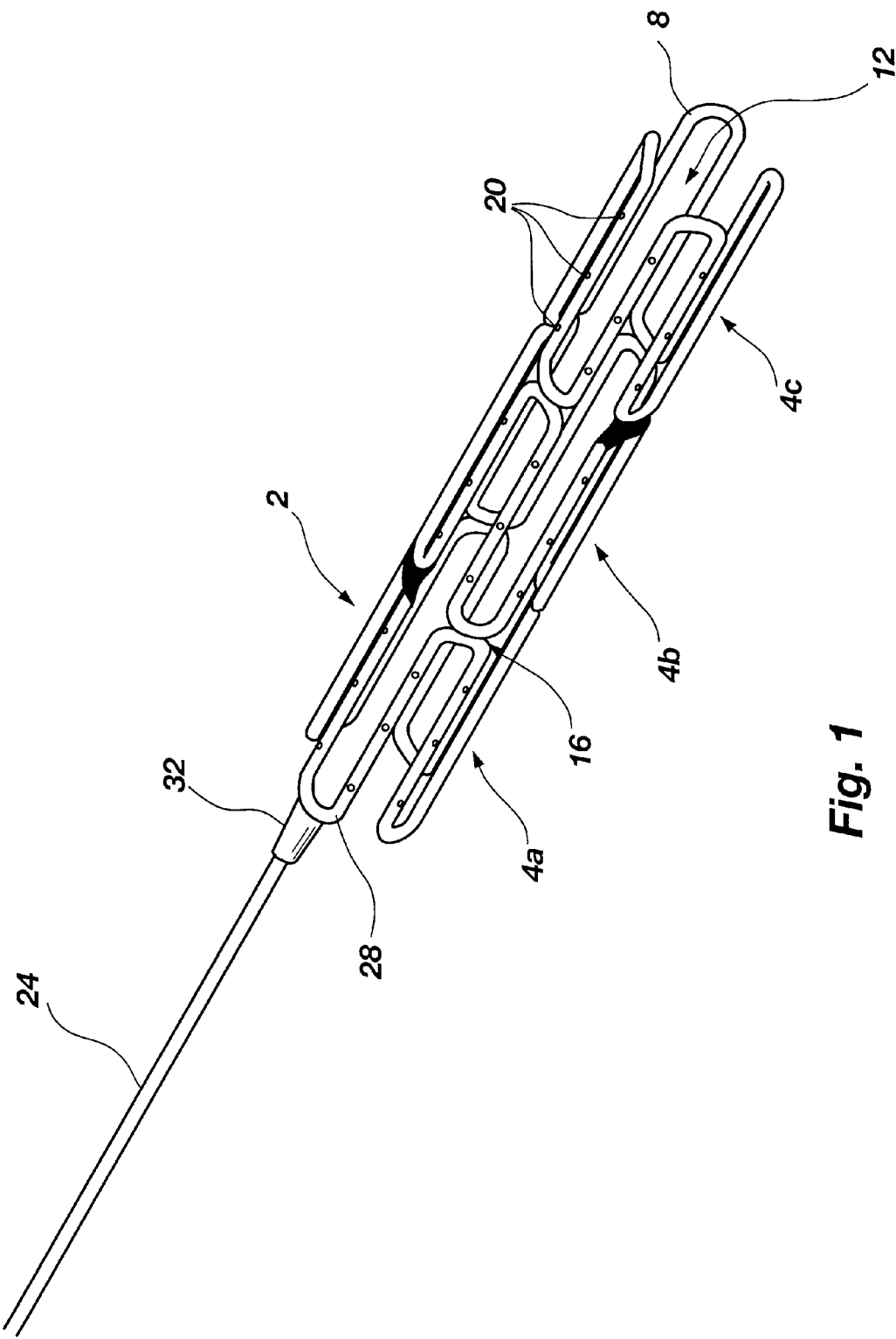
FIG. 1 is a perspective, fragmented view of a detachable stent with drug delivery capabilities, in accordance with the principles of the present invention.

Referring to FIG. 1, there is shown a perspective, fragmented view of one embodiment of a stent 2 made in accordance with the present invention. The stent 2 includes three lattice sections 4a, 4b and 4c, stacked end to end as shown. Each lattice section is composed of an elongate, hollow flexible wire 8 formed into a generally gathered annular lattice having a central void 12. In this case, the wire 8 is formed generally of a zig-zag configuration circumferentially about the void 12, again as shown.

The three lattice sections 4a, 4b and 4c are joined together end to end by adhesive, welding, brazing or similar joining method. The locations at which the lattice sections are joined, such as joint 16, allow for communication between the hollows of the wires of the joined sections. This could be done by simply forming holes in each of the wires at the precise location of joining so that the hollows of each of the wires were in communication with one another through the holes. Alternatively, a continuous piece of tubing could be formed into a unitary stent, eliminating the need for joining the separate sections.

The hollow wires of the lattice sections 4a, 4b and 4c include a plurality of apertures 20 which face generally outwardly of the respective lattice and through which medication may flow from the hollow of the respective wires thereout.

A hollow connecting wire 24 is coupled to the wire of lattice 4a at a bend location 28 for example by welding, brazing or an appropriate adhesive (or could be formed of a single continuous hollow wire). The coupling is made so that the hollow of the connecting wire 24 joins or communicates with the hollow of the wire of lattice 4a. Formed near or at the coupling location is a discontinuity 32 to provide a breaking or detachment point for detaching the lattice sections 4a, 4b and 4c from the connecting wire 24. The discontinuity 32 could take a variety of forms including a narrowing of the wire, a solder joint, a section of weaker wire material, a section with selectively placed cuts, a spot weld, or a section with chemically or thermally changed properties, which when perturbed by a perturbation signal, will cause the wire 24 to sever at the discontinuity and allow separation of the lattice sections 4a, 4b and 4c. The perturbation signal advantageously is an ultrasonic signal transferred down the wire 24 to cause mechanical separation at the location of the discontinuity. See copending patent application Ser. No. 09/023,806 filed Feb. 13, 1998, for additional discussion of mechanisms for detaching one portion of a wire from another portion, said application being incorporated herein by reference.

Advantageously, the connecting wire 24 and the wires from which the lattice sections 4a, 4b and 4c are made, are constructed of stainless steel, platinum or nickel-titanium alloy. The outside diameter of such wire illustratively is 0.008 inches, with the inside diameter being 0.004 inches.

Use of the stent of FIG. 1 may best be understood by referring to FIG. 2A which shows a balloon catheter 36 disposed in the hollow 12 of the stent 2. The balloon catheter 36 is of conventional design and includes an expandable bladder or balloon 36a disposed about a conventional guide wire 40. The balloon catheter 36 also includes a catheter portion 36b connected to a proximal end of the balloon 36a, to carry saline, contrast or other fluid from a source 44 to inflate the balloon 36a. The guide wire 40 extends not only through the balloon portion 36a at the balloon catheter 36 but also through the catheter portion 36b and is used to guide the balloon catheter 36 with stent 2 in place over the balloon portion 36a, to a target location. In particular, the guide wire 40 would be inserted into a blood vessel (together with the catheter) having a lesion or other vascular defect, until the terminal end of the guide wire reached the target site. The balloon catheter 36, with stent positioned in place about the balloon portion 36a, would then be placed over the guide wire 40 and moved to the target site (or may be loaded onto the guide wire at initial insertion). The balloon portion 36a of the balloon catheter 36 would then inflated be by the inflation source 44 to spread apart the stent 2 to contact and spread apart the blood vessel walls at the target site.

The configuration of the lattice sections 4a, 4b and 4c allow for the spreading apart of the sections under pressure from the balloon section 36a, to contact and similarly spread apart the blood vessel walls, as shown in FIG. 2B. Since the wires of the lattice sections 4a, 4b and 4c are made of a flexible but non-elastic material, such as stainless steel, once the sections have been expanded as illustrated in FIG. 2B, they will remain in the expanded condition even after the balloon section 36a is deflated.

The next step in the treatment process is to deflate the balloon section 36a of the balloon catheter 36 and then remove the balloon catheter from the central void of the stent 2 and from the blood vessel in question. Next, medication from a medication source 48, such as syringe, is supplied via connecting wire 24 to the lattice sections 4a, 4b and 4c, to flow out through the apertures 20 and into contact with the expanded vessel walls (or into areas adjacent the stent, which will be discussed momentarily). Examples of medications which might be supplied and diseases which might be treated include Abciximals, gene therapy agents, Heparin, Urokinase, and antimytotics for treating clotting, restenosis and smooth muscle cell proliferation.

As an alternative to deflating the balloon catheter 36 and removing it from the void 12 of the stent 2 before supplying the medication, would be to leave the expanded balloon portion 36a in place while supplying the medication to the lattice sections 4a, 4b and 4c. Also, a perfusion balloon could be used in this circumstance to provide for longer therapies.

After medication has been supplied to the stent 2 and ultimately the vessel walls or the therapy is otherwise complete, the stent is detached from the connecting wire 24 by applying a perturbation signal from a signal source 52, as described in the afore-cited patent application. After detachment, the connecting wire 24 and guide wire 40 are removed from the blood vessel, leaving the stent 2 in place in the vessel in the expanded condition, to maintain the vessel walls apart.

Although the stent of FIGS. 1 and 2 had been described for serving both as a stent to hold vessel walls apart and as a drug delivery device, the stent could simply be used to hold the vessel walls apart without the attendant drug or medication delivery, in which case the stent need not be hollow. The advantage of placing the stent and expanding it before detachment of the connecting wire 24 is that the stent is much less likely to be inadvertently separated from the balloon portion 36a of the balloon catheter 36 during insertion and expansion or enlargement of the stent. Of course, stents which do become separated could migrate in the blood vessel to a location where the stent could either clog the flow of blood in the blood vessel or otherwise damage the blood vessel or other body organs.

Figure 3:
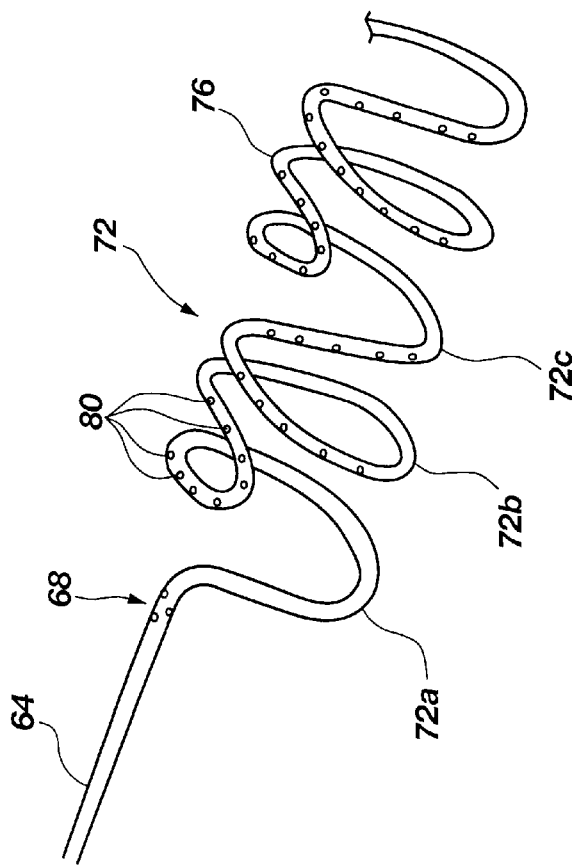
FIG. 3 is a perspective, fragmented view of an alternative embodiment of a detachable, balloon expandable stent, in accordance with the present invention.

FIG. 3 is a perspective view of another embodiment of the present invention. In this embodiment, a tubular connecting wire 64 is joined through a discontinuity 68 to a proximal end of a tubular coil lattice 72. The lattice 72 is constructed of a hollow wire 76, formed in a first helical turn 72a which then bends to extend in the opposite direction in a second helical turn 72b which then, again, bends to extend in the same direction as the first helical turn to form a third helical turn 72c, etc. Openings 80 are formed on the outside of the wire 76 (or other locations as will be discussed) forming the lattice to allow delivery of medication to vessel walls of the vessel in which the lattice 72 is deployed, as discussed earlier for the embodiment of FIGS. 1 and 2. A balloon catheter would be used, as also discussed earlier to expand the helic 72 after positioning of the target site, medication would then be supplied to treat the target vessel walls, etc.

Figure 4A:
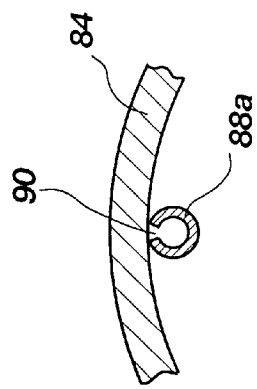
FIGS. 4A–4C are cross sectional end views of blood vessels with stents showing various positions of perforations in the stents.
Figure 4B:
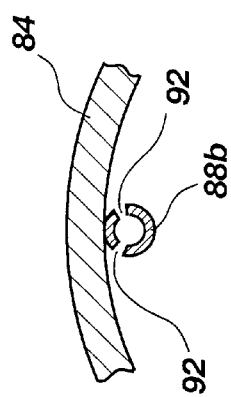
Figure 4C:
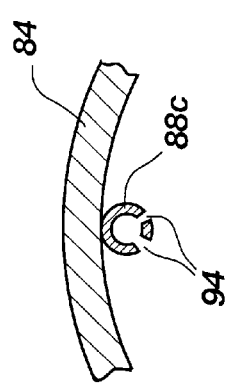

FIGS. 4A, 4B and 4C show a fragmented, cross-sectional view of a vessel wall 84 with a hollow wire 88a, 88b and 88c respectively, having openings or perforations positioned in different locations. In FIG. 4A, the openings 90 positioned on the outside, directly against the vessel wall; in FIG. 4B, the openings 92 are positioned toward the outside but not directly against the vessel wall; and FIG. 4C, the openings 94 are positioned toward the inside of the wire (which would allow for more gradual, less concentrated drug delivery therapy for the vessel wall).

It is to be understood that the above-described arrangements are only illustrative of the principles of the present invention. Numerous modifications and alternative arrangements may be devised by those skilled in the art without departing from the spirit and scope of the present invention and the appended claims are intended to cover such modifications and arrangements.

What is claimed is:

1. A stent for disposition in a body passageway to allow delivery of a solution to the passageway walls, said stent comprising an elongate, hollow flexible wire, a distal end of which is formed into a generally gathered annular lattice with a central void, extending from a dispatch location of the wire, for disposition at a target location in the passageway, said lattice including perforations through which solution may flow from the hollow of the wire, said wire further including a discontinuity located generally at or near the dispatch location, means for mechanically stimulating the wire to cause detachment of the lattice at the discontinuity, an expandable balloon disposed in the void of the lattice which, when expanded, forces the lattice outwardly to contact the passageway walls at the target location, and means for selectively expanding and contracting the balloon.

2. A stent as in claim 1 wherein the wire is made of stainless steel.

3. A stent as in claim 2 wherein the outside diameter of the wire is about 0.008 inches or less.

4. A stent as in claim 1 wherein said lattice is formed generally of a zig-zag configuration circumferentially about the void.

5. A stent as in claim 1 wherein said lattice is formed generally of a coil configuration circumferentially about the void.

6. A stent as in claim 5 wherein said coil configuration comprises a length of wire alternately coiled about the void, approximately one turn in a first direction and then approximately another turn in the opposite direction, etc.

7. A stent as in claim 1 further including means attachable to a proximal end of the wire for supplying a solution to the hollow of the wire for transport to and out the perforation in the lattice.

8. A stent as in claim 1 wherein said perforations are formed in the wire to generally face the passageway walls.

9. A stent as in claim 1 wherein said perforations are formed in the wire to generally face inwardly of the passageway walls.

10. A stent for disposition in a duct to maintain the duct walls apart to allow the flow of fluid therethrough, said stent comprising an elongate flexible support wire formed into an annular lattice having a central void, for disposition at a target location in the duct, an elongate flexible connecting wire joined at a distal end to the annular lattice and having a discontinuity for severing when supplied with a mechanical perturbation signal, a balloon catheter having an expandable section disposable in the void of the annular lattice so that when the expandable section is expanded, it forces the annular lattice radially outwardly to contact and hold apart the duct walls, means for selectively expanding the expandable section of the balloon catheter, and means for supplying a mechanical perturbation signal to the discontinuity of the connecting wire to cause severance thereof.

11. A stent as in claim 10 wherein the discontinuity comprises a narrowed portion of the wire, and wherein the perturbation signal supplying means comprises an ultrasonic signal generator.

12. A stent as in claim 10 wherein the discontinuity comprises a portion of the wire made from a material different from the material of the rest of the wire, and wherein the perturbation signal supplying means comprises an ultrasonic signal generator.

13. A stent as in claim 10 wherein the discontinuity comprises one or more cuts in the wire, and wherein the perturbation signal supplying means comprises an ultrasonic signal generator.

14. A stent as in claim 10 wherein the discontinuity comprises a spot weld, and wherein the perturbation signal supplying means comprises an ultrasonic signal generator.

15. A stent as in claim 10 wherein the support wire and connecting wire are tubular having central hollows which are in communication, wherein the lattice includes a plurality of openings through which medication may flow from the hollow of the support wire forming the lattice, said stent further including means for selectively supplying medication to the hollow of the connecting wire to flow to the hollow of the support wire and out the openings.

16. A stent as in claim 15 wherein the openings are positioned to face generally outwardly of the lattice.

17. A stent as in claim 10 wherein the wires are made of a material selected from the group consisting of stainless steel, platinum, platinum alloys and nickel-titanium alloy.

18. A stent system for disposition in a body duct to maintain the duct walls apart, said stent system comprising:

a generally tubular-shaped stent for disposition at a target location in the duct, an elongate flexible connecting wire joined at a distal end to the stent for preventing unwanted migration of the stent, said wire including a discontinuity for severing when supplied with a mechanical perturbation signal, and means for supplying a mechanical perturbation signal to the discontinuity of the connecting wire to cause severance thereof.

19. A stent system as in claim 18 further including means for selectively expanding the stent radially outwardly to contact and hold apart the duct walls.

20. A stent system as in claim 18 wherein the stent comprises an elongate flexible support wire formed into an annular lattice.

21. A stent system as in claim 18 wherein the support wire and connecting wire are tubular having central hollows which are in communication, wherein the lattice includes a plurality of openings through which the medication may flow from the hollow of the support wire forming the lattice, said stent system further including means for selectively supplying medication to the hollow of the connecting wire to flow to the hollow of the support wire and out the openings.

* * * * *